United States Patent [19]

Stölzer

[11] 4,394,309
[45] Jul. 19, 1983

[54] PROCESS FOR THE PREPARATION OF N,N-DIMETHYL-N-(2-BROMO-4-METHYL-PHENYL)-TRIAZENE

[75] Inventor: Claus Stölzer, Wuppertal, Fed. Rep. of Germany

[73] Assignee: Bayer Aktiengesellschaft, Leverkusen, Fed. Rep. of Germany

[21] Appl. No.: 249,247

[22] Filed: Mar. 30, 1981

[30] Foreign Application Priority Data

Apr. 12, 1980 [DE] Fed. Rep. of Germany ....... 3014122

[51] Int. Cl.³ ................ C07C 113/00; C07C 113/04; C07C 103/27; C07C 87/60
[52] U.S. Cl. .................................... 260/140; 260/141; 564/210; 564/211; 564/414
[58] Field of Search ................ 260/140; 564/210, 211, 564/414

[56] References Cited

U.S. PATENT DOCUMENTS 2,828,299 3/1958 Von Glahn et al. ................ 260/140
2,842,535 7/1958 Lowenfeld et al. ................ 260/140
3,162,571 12/1964 Adams et al. ................... 260/140 X
3,206,357 9/1965 Cannon et al. ................. 260/140 X

FOREIGN PATENT DOCUMENTS 2652810 5/1978 Fed. Rep. of Germany ...... 260/140

OTHER PUBLICATIONS

Justus Lieberg's, "Amalen der Chemie vol. 253 (1886)", pp. 254–271, (Wallach).
"Organic Syntheses Collective vol. 1", pp. 111–113, (Johnson et al.).
"Sull'Attivita Fitotossica Di Derivati Triazenici", pp. 129–132, 143, 148, (Mazza et al.).

*Primary Examiner*—Floyd D. Higel
*Attorney, Agent, or Firm*—Sprung, Horn, Kramer & Woods

[57] ABSTRACT

A process for the preparation of N,N-dimethyl-N'-(2-bromo-4-methyl-phenyl)-triazene of the formula

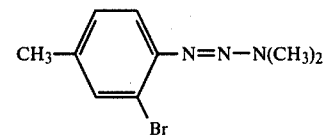

comprising
(a) reacting N-acetyl-p-toluidine of the formula

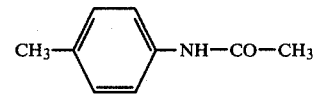

with bromine at a temperature between about 0° and 100° C., to give the intermediate product of the formula

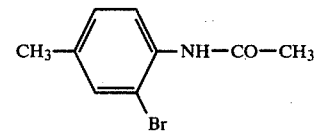

(b) reacting the intermediate product with hydrochloric acid by either
  (i) adding a dilute solution of aqueous hydrochloric acid to the intermediate product in its reaction solution and heating the mixture to a temperature between about 50° and 120° C., or
  (ii) precipitating the intermediate product from its reaction solution by mixing with water and filtering off, and without purification or drying heating the precipitate with dilute aqueous hydrochloric acid to a temperature between about 50° and 120° C., thereby to form a solution of 2-bromo-4-methylaniline hydrochloride, (c) reacting the resulting aqueous solution with an alkali metal nitrite at a temperature between about −20° and +30° C., and (d) reacting the product with dimethylamine at a temperature between about 0° and 50° C.

9 Claims, No Drawings

PROCESS FOR THE PREPARATION OF N,N-DIMETHYL-N-(2-BROMO-4-METHYL-PHENYL)-TRIAZENE

The invention relates to an unobvious process for the preparation of N,N-dimethyl-N'-(2-bromo-4-methyl-phenyl)-triazene, which is known.

It is known that N,N-dialkyl-N'-aryl-triazenes, such as N,N-dimethyl-N'-(2-bromo-4-methyl-phenyl)-triazene, are obtained when diazonium salts derived from aromatic amines, such as 2-bromo-4-methyl-benzene-diazonium chloride, are reacted with secondary amines, such as dimethylamine (see Il Farmaco, Ed. Sci 29 (1974), 129–148—Chem. Abstr. 81 (1974), 34417 d).

In individual cases, however, the corresponding aromatic amines from which the diazonium salts are derived are only obtained via multi-stage processes, unsatisfactory yields being achieved overall. Thus, for example, 2-bromo-4-methyl-aniline is prepared by acetylating p-toluidine with acetic acid, reacting the acetylation product with bromine, isolating the intermediate product and saponifying it by reaction with hydrochloric acid, isolating the hydrochloride of the saponification product and liberating 2-bromo-4-methyl-aniline therefrom with sodium hydroxide solution. The overall yield is between 60 and 67% of theory (see Org. Synthese Coll. volume I (1932), 111–113).

The present invention now provides a process for the preparation of N,N-dimethyl-N'-(2-bromo-4-methyl-phenyl)-triazene of the formula

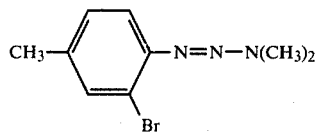

(I)

in which, in a first stage, N-acetyl-p-toluidine of the formula

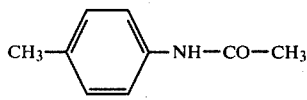

(II)

is reacted with bromine, if appropriate in the presence of an acid acceptor and if appropriate in the presence of a diluent, at a temperature between about 0° and 100° C., to give the intermediate product of the formula

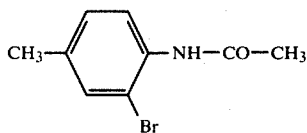

(III)

which, in a second stage, is reacted with hydrochloric acid by either (a) adding a dilute solution of aqueous hydrochloric acid to the intermediate product of the formula (III) in its reaction solution and heating the mixture to a temperature between about 50° and 120° C., or (b) precipitating the intermediate product of the formula (III) from its reaction solution by mixing with water and filtering off, and heating with dilute aqueous hydrochloric acid to a temperature between about 50° and 120° C., without purification or drying, and, in both cases (a) and (b), the 2-bromo-4-methylaniline hydrochloride contained in the resulting aqueous solution is thereafter reacted with an alkali metal nitrite at a temperature between about −20° and +30° C., and, finally, the product is reacted with dimethylamine, if appropriate in the presence of an acid-binding agent, at a temperature between about 0° and 50° C. If desired, the reaction solution of the intermediate of the formula (III) may be treated with a reducing agent prior to step (a) or (b).

It is surprising that N,N-dimethyl-N'-(2-bromo-4-methyl-phenyl)-triazene can be obtained in a high yield and a good purity by the process according to the invention, since it had to be expected that if the hitherto necessary isolation and purification steps were omitted, losses in yield would be obtained as a result of side reactions and the end product would be highly contaminated.

The reactions which proceed in the process according to the invention are illustrated in the following reaction scheme.

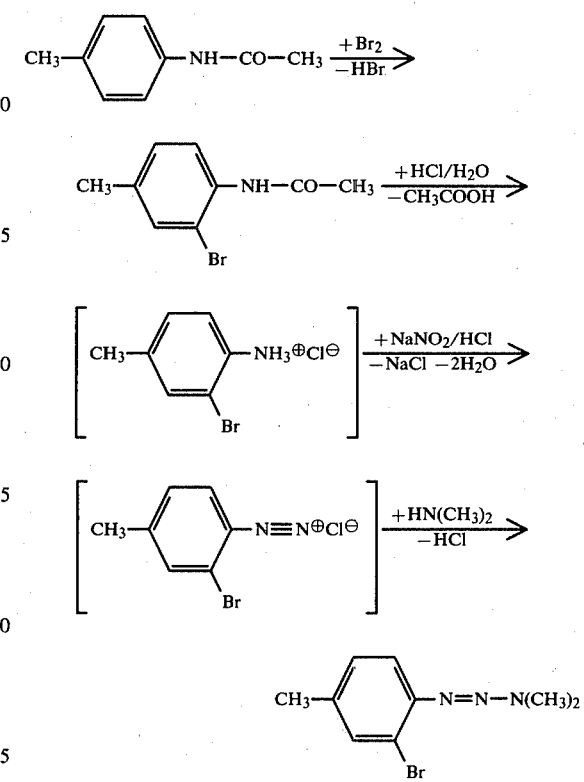

The N-acetyl-p-toluidine to be employed as the starting substance is a commerically available product.

The process according to the invention is preferably carried out in the presence of a water-miscible organic diluent which is relatively inert towards bromine. Aliphatic carboxylic acids, such as, formic acid, acetic acid and propionic acid, are particularly suitable. Acetic acid is particularly preferred as the diluent for the first stage of the process. If appropriate, water is additionally used as a second solvent component. In general, water is used as the solvent in the second stage.

The customary acid-binding agents can be used as acid acceptors. Acid-binding agents which are particularly suitable are alkali metal hydroxides (such as sodium hydroxide and potassium hydroxide), alkali metal carbonates and bicarbonates (such as sodium carbonate and bicarbonate and potassium carbonate and bicarbonate), alkali metal acetates and formates (such as sodium acetate and formate), and ammonia and amines (such as triethylamine).

In the first stage of the process the reaction temperature can be varied within the substantial range of about 0° to 100° C., preferably about 10° to 80° C. The process according to the invention is in general carried out under normal pressure.

Per mole of N-acetyl-p-toluidine, about 1 to 1.5 moles, preferably about 1.05 to 1.3 moles, of bromine are employed in the first stage and about 2 to 5 moles, preferably about 2.5 to 4 moles, of hydrochloric acid containing hydrogen chloride, about 0.9 to 1.2 moles, preferably about 0.95 to 1.1 moles, of alkali metal nitrite and about 1 to 3 moles, preferably about 1.5 to 2 moles, of dimethylamine are employed in the second stage.

In a preferred embodiment of the process according to the invention, N-acetyl-p-toluidine in one of the abovementioned solvents or in a mixture thereof is initially introduced into the reaction vessel, if appropriate under an inert gas atmosphere, such as under nitrogen, in the first stage, and one of the abovementioned acid acceptors, if appropriate in aqueous solution, and bromine are slowly added successively.

After stirring the mixture for about one hour, it is diluted, if appropriate, with water and, if appropriate, a reducing agent is added until the reaction mixture becomes colorless. The product of the formula (III), which is obtained as crystals, is separated off by filtration, but is not further purified or dried.

Reducing agents which can be used are compounds which are suitable for removing excess bromine by reduction. Examples of these compounds which may be mentioned are sulphur dioxide, sulphurous acid and salts thereof, such as sodium sulphite and bisulphite and potassium sulphite and bisulphite.

For carrying out the second stage of the process, the still moist intermediate product of the formula (III) is heated with dilute aqueous hydrochloric acid, the hydrogen chloride content of which is between about 1 and 10 percent by weight, to temperatures from about 50° to 120° C., preferably about 80° to 110° C., for some hours. After cooling the mixture to temperatures from about −20° to +30° C., preferably from about −10° to +15° C., a saturated aqueous alkali metal nitrite solution (which preferably contains sodium nitrite) is then slowly metered in and, after subsequently stirring this reaction mixture for a short time, it is added to an aqueous solution of dimethylamine and, if appropriate, one of the abovementioned acid-binding agents at temperatures from about 0° to 50° C., preferably from about 10° to 40° C.

After stirring the mixture for about one hour, the product of the formula (I), which is obtained as crystals, is isolated by filtration.

The N,N-dimethyl-N'-(2-bromo-4-methyl-phenyl)-triazene to be prepared by the process according to the invention is known as a phytotoxic, that is to say herbicidal, product (see Il Farmaco, Ed. Sci. 29 (1974), 129–148—Chem. Abstr. 81 (1974), 34417 d).

However, the compound of the formula (I) can also be used as an intermediate product for the preparation of insecticidally active pyrethroids:

For this preparation, the triazene is reacted with hydrogen fluoride at temperatures between −20° and +150° C. and the 3-bromo-4-fluorotoluene thereby obtained is purified, if appropriate, by distillation and reacted with sodium phenolate or potassium phenolate in the presence of copper or a catalytically active copper compound, such as copper oxide, and in the presence of a diluent, such as N,N-dimethylacetamide, at a temperature between 120° and 180° C. The 3-phenoxy-4-fluorotoluene which can be obtained in this manner and can be purified by distillation is already known as an intermediate product for pyrethroids (see U.S. Pat. No. 4,218,469, issued Aug. 19, 1980).

The process of the present invention is illustrated by the following example:

EXAMPLE

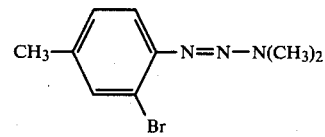

300 g of acetic acid were initially introduced into a reaction vessel which was flushed with nitrogen, and 100 g of N-acetyl-p-toluidine were added in portions at 20° C., while stirring. The mixture was then warmed to 50° C. for about 2 hours.

90 g of 45% strength sodium hydroxide solution and 130 g of bromine were then slowly added successively to the reaction mixture at 50° to 55° C., while stirring, and, when the addition had ended, the mixture was subsequently stirred for about a further 1 hour at 50° C.

The reaction mixture was then diluted with 1 liter of water, and a saturated aqueous solution of 16 g of sodium bisulphite was then added. The intermediate product which had crystallized out was filtered off and the still moist intermediate product from the filter was introduced into a reaction vessel into which 2 liters of water had first been introduced. The mixture was warmed to 80° C., while stirring, and 233 g of 30% strength hydrochloric acid were metered in over a period of 30 minutes. The reaction mixture was then heated to the boiling point under reflux for 3 hours.

After cooling the mixture to 0° C., a saturated aqueous solution of 45.5 g of sodium nitrite was added thereto at 0° to 5° C. in the course of 1 hour and the mixture was then subsequently stirred at this temperature for about 30 minutes. The reaction mixture was then introduced into another reaction vessel, into which 222.5 g of sodium carbonate and 77.5 g of dimethylamine in 640 ml of water had been initially introduced and in which the internal temperature was kept at 15° to 25° C.

After stirring for a further hour, the product was isolated by pressure filtration, washed three times with 800 ml of water each time and dried at 30° C. under reduced pressure.

N,N-Dimethyl-N'-(2-bromo-4-methyl-phenyl)-triazene was obtained in a yield of 146 g (90% of theory, relative to N-acetyl-p-toluidine employed).

It will be appreciated that the instant specification and examples are set forth by way of illustration and not limitation, and that various modifications and changes may be made without departing from the spirit and scope of the present invention.

I claim:

1. A process for the preparation of N,N-dimethyl-N'-(2-bromo-4-methyl-phenyl)-triazene of the formula

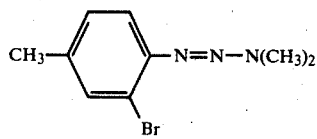

consisting essentially of
(a) reacting N-acetyl-p-toluidine of the formula

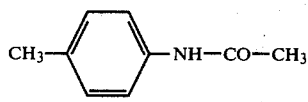

with bromine at a temperature between about 0° and 100° C., to give the intermediate product of the formula

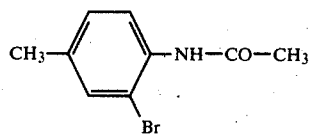

(b) reacting the intermediate product with hydrochloric acid by either
(i) adding a dilute solution of aqueous hydrochloric acid to the intermediate product in its reaction solution and heating the mixture to a temperature between about 50° and 120° C., or
(ii) precipitating the intermediate product from its reaction solution by mixing with water and filtering off, and without purification or drying heating the precipitate with dilute aqueous hydrochloric acid to a temperature between about 50° and 120° C., thereby to form a solution of 2-bromo-4-methylaniline hydrochloride,
(c) reacting the resulting aqueous solution with an alkali metal nitrite at a temperature between about −20° and +30° C., and
(d) reacting the product with dimethylamine at a temperature between about 0° and 50° C.

2. A process according to claim 1, in which step (a) is carried out in the presence of an acid acceptor.

3. A process according to claim 1, in which step (a) is carried out in the presence of a diluent.

4. A process according to claim 3, in which the diluent is acetic acid or an acetic acid/water mixture.

5. A process according to claim 1, in which the reaction solution of the intermediate of step (a) is treated with a reducing agent prior to step (b).

6. A process according to claim 1, in which step (a) is carried out at a temperature between about 10° and 80° C.

7. A process according to claim 1, in which, per mole of N-acetyl-p-toluidine, between about 1.05 and 1.3 moles of bromine are employed in step (a), and in step (b) between about 2.5 and 4 moles of hydrochloric acid containing hydrogen chloride, between about 0.95 and 1.1 moles of alkali metal nitrite and between about 1.5 and 2 moles of dimethylamine.

8. A process according to claim 1, in which the reaction with dimethylamine is carried out in the presence of an acid binding agent.

9. A process according to claim 7, in which step (a) is carried out at a temperature between about 10° and 80° C. in the presence of an acid acceptor and acetic acid or an acetic acid/water mixture as a diluent, the reaction solution of the intermediate of step (a) is treated with a reducing agent prior to step (b), and the reaction with dimethylamine is carried out in the presence of an acid binding agent.

* * * * *